United States Patent [19]

Woods

[11] 4,234,592
[45] Nov. 18, 1980

[54] ALKYLTHIODIAZATRITHIAPENTALENE COMPOSITIONS AND METHODS OF USING AS PLANT DISEASE CONTROL AGENTS, INSECTICIDES, AND LARVICIDES

[75] Inventor: Thomas S. Woods, Wilmington, Del.

[73] Assignee: E. I. Du Pont de Nemours and Company, Wilmington, Del.

[21] Appl. No.: 42,944

[22] Filed: May 29, 1979

[51] Int. Cl.³ .................... A01N 43/90; C07D 513/04
[52] U.S. Cl. ..................................... 424/270; 548/123
[58] Field of Search ................. 260/306.8 F; 548/123; 424/270

[56] References Cited

PUBLICATIONS

Goerdeler, J., "Chem. Ber." 109, 3108 (1976).
Haynes, J. W.; ARS–Southern Region, 1976.
Haynes, J. W.–"Chem. Ber.", 97, 2567 (1964).
Burger, A. "Medincinal Chem.", 2nd ed., Interscience Publishers, New York, 1960, pp. 1053–1056.

Primary Examiner—Donald G. Daus
Assistant Examiner—Lisa Jones

[57] ABSTRACT

Compounds of the formula:

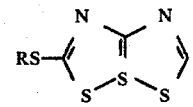

wherein
R is alkyl, alkenyl or cycloalkyl optionally substituted with chlorine, cycloalkylalkyl and $(CH_2)_n R'$
wherein
n is 1–3 and
R' is phenyl optionally substituted with $CH_3$, $CH_3O$, $NO_2$ or 1–2 halogens are useful to control a broad range of fungus diseases and insect and larval pests.

50 Claims, No Drawings

ALKYLTHIODIAZATRITHIAPENTALENE COMPOSITIONS AND METHODS OF USING AS PLANT DISEASE CONTROL AGENTS, INSECTICIDES, AND LARVICIDES

BACKGROUND OF THE INVENTION

This invention relates to certain alkylthiodiazatrithiapentalenes and their use as broad spectrum fungicides or fungistats which can prevent and/or mitigate the damage caused by a variety of fungus diseases to plants, warm-blooded animals and organic materials. The compounds of this invention are also effective in controlling insects and larval pests.

J. Goerdeler, et al., Chem. Ber., 109, 3108 (1976) teaches the preparation of compounds of the general formula

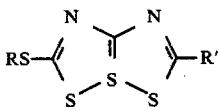

wherein
R can be $CH_3$, $C_2H_5$, $i-C_3H_7$, $n-C_6H_3$, $C_6H_5CH_2$ or $p-CH_3C_6H_4$ and R' can be H.

There is no utility taught for the compounds of the reference.

Other references such as J. W. Haynes, et al. in reports of the U.S. Agricultural Research Service, Southern Region, 1976, ARS-S-131 and Chem. Ber., 97, 2567 (1964) disclose structurally similar compounds wherein the R and/or R' substituents are attached to the dithiazolodiathiazole rings through a nitrogen atom. It is indicated in Haynes, et al., that the compounds were tested as boll weevil chemosterilants. No other utility is suggested by the references.

According to the instant invention, compounds have been discovered which are highly active against a variety of plant fungus diseases and insect and larval pests.

SUMMARY OF THE INVENTION

This invention relates to compounds of Formula I, some of which are not novel, and to agricultural compositions containing them and to the methods of using these compounds as fungicides, fungistats, insecticides and larvicides.

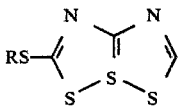

wherein
R is alkyl of $C_1-C_{10}$, optionally substituted with 1-2 chlorines; alkenyl of $C_3-C_8$, optionally substituted with 1-2 chlorines; cycloalkyl of $C_3-C_{10}$; cycloalkylalkyl of $C_6-C_9$; and $(CH_2)_nR'$, wherein n is 1-3 and R' is phenyl, optionally substituted with $CH_3$, $CH_3O$, $NO_2$, or 1-2 fluorines, chlorines, or bromines.

Preferred for economical and/or for reasons of higher biological activity are the following groups of compounds of Formula I:
(1) Those compounds where R is alkyl of $C_2-C_8$.
(2) Those wherein R is alkenyl of $C_3-C_6$.
(3) Those wherein R is cycloalkyl of $C_3-C_8$.
(4) Those wherein R is $(CH_2)_nR'$ wherein n is 1 or 2.
(5) Those of Group 4 wherein R' is phenyl optionally substituted with 1-2 chlorines.

More preferred for ease of synthesis and/or cost are:
(6) Those compounds of formula I wherein R is alkyl of $C_2-C_6$.
(7) Those wherein R is alkenyl of $C_3-C_5$.
(8) Those wherein R is cycloalkyl of $C_5-C_7$.
(9) Those compounds of Group 5 wherein R' is phenyl optionally substituted with one chlorine.

Most preferred for biological activity and cost are:
(10) Those compounds of formula I wherein R is alkyl of $C_2-C_3$.
(11) Those wherein R is $C_3$ or $C_4$ alkenyl.
(12) Those wherein R is cycloalkyl of $C_5-C_6$.
(13) Those compounds of Group (9) wherein R' is phenyl.

Specifically preferred for their outstanding biological activity and/or very favorable cost or both are:
2-[(1-methylethyl)thio] [1,2,4]-dithiazolo[1,5-b] [1,2,4]-dithiazole-4-$S^{IV}$
2-(ethylthio) [1,2,4]-dithiazolo[1,5-b] [1,2,4]-dithiazole-4-$S^{IV}$
2-[(phenylmethyl)thio] [1,2,4]-dithiazolo-[1,5-b] [1,2,4]-dithiazole-4-$S^{IV}$
2-(cyclohexylthio) [1,2,4]-dithiazolo-[1,5-b] [1,2,4]-dithiazole-4-$S^{IV}$
2-[(phenylethyl)thio] [1,2,4]-dithiazolo-[1,5-b] [1,2,4]-dithiazole-4-$S^{IV}$
2-(cyclopentylthio) [1,2,4]-dithiazolo-[1,5-b] [1,2,4]-dithiazole-4-$S^{IV}$
2-[(2-methyl-2-propenyl)thio] [1,2,4]-dithiazolo-[1,5-b]-[1,2,4]-dithiazole-4-$S^{IV}$.
2-(propylthio) [1,2,4]-dithiazolo[1,5-b] [1,2,4]-dithiazole-4-$S^{IV}$
2-(butylthio) [1,2,4]-dithiazolo[1,5-b] [1,2,4]-dithiazole-4-$S^{IV}$
2-[(3-methylbutyl)thio]-dithiazolo[1,5-b] [1,2,4]-dithiazole-4-$S^{IV}$
2-[(2-methylpropyl)thio]-dithiazolo[1,5-b] [1,2,4]-dithiazole-4-$S^{IV}$.

This invention also relates to novel compounds of Formula I

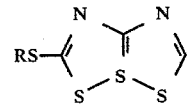

wherein
R is alkyl of $C_2-C_{10}$ substituted with 1-2 chlorines; alkenyl of $C_3-C_8$, optionally substituted with 1-2 chlorines; cycloalkyl of $C_3-C_{10}$; cycloalkylalkyl of $C_6-C_9$; and $(CH_2)_nR'$ wherein n is 2 or 3 and R' is phenyl, optionally substituted with $CH_3$, $CH_3O$, $NO_2$, or 1-2 fluorines, chlorines, or bromines.

Preferred for reasons of higher biological activity, ease of synthesis and/or favorable cost are the following groups of compounds of Formula II;
(1) Those compounds wherein R is alkyl of $C_2-C_6$ substituted with 1-2 chlorines.
(2) Those compounds wherein R is alkenyl of $C_3-C_6$, optionally substituted with 1-2 chlorines.
(3) Those wherein R is cycloalkyl of $C_3-C_8$.
(4) Those wherein R is cycloalkylalkyl of $C_6-C_8$.
(5) Those wherein R is $(CH_2)_nR'$, n is 2 and R' is phenyl, optionally substituted with 1-2 chlorines.

More preferred for ease of synthesis and/or cost are:

(1) Those compounds of formula II wherein R is alkenyl of $C_3$–$C_5$, optionally substituted with 1–2 chlorines.
(2) Those wherein R is cycloalkyl of $C_5$–$C_7$.
(3) Those novel compounds of Group 4 wherein R' is phenyl, optionally substituted with one chlorine.

Most preferred on the basis of biological activity and/or cost are:
(1) Those compounds of formula II wherein R is alkenyl of $C_3$–$C_4$.
(2) Those wherein R is cycloalkyl of $C_5$–$C_6$.
(3) Those novel compounds of Group (3) wherein R' is phenyl.

Specifically preferred for their outstanding biological activity and/or very favorable cost or both are:

2-(cyclohexylthio) [1,2,4]-dithiazolo-[1,5-b] [1,2,4]-dithiazole-4-$S^{IV}$

2-[(2-phenylethyl)thio] [1,2,4]-dithiazolo-[1,5-b] [1,2,4]-dithiazole-4-$S^{IV}$ 2-(cyclopentylthio) [1,2,4]-dithiazolo-[1,5-b] [1,2,4]-dithiazole-4-$S^{IV}$ 2-[(2-methyl-2-propenyl)thio] [1,2,4]-dithiazolo-[1,5-b]-[1,2,4]-dithiazole-4-$S^{IV}$.

DETAILED DESCRIPTION OF THE INVENTION

Preparation

Compounds of this invention (3) can be prepared by suitable modification of the method taught by Goerdeler, et al., Chem. Ber., 109, 3108 (1976), the teachings of which are incorporated herein by reference, as shown in equation A.

$$\text{RSSCHCl}_2 + 2\text{MSCN} \xrightarrow{\Delta} \text{RS-}\underset{(3)}{\underbrace{\text{[dithiazolo ring]}}}$$

(1)      (2)      (3)

Equation A where M is an alkali metal such as sodium or potassium

An alkyl dichloromethyl disulfide (1) is mixed with at least two molar equivalents of dry alkali metal thiocyanate (2) in a suitable solvent, such as acetonitrile, and the mixture is heated at 50°–100° C. until the reaction is complete, as is illustrated in Example 1.

The starting materials (1) can be made by mixing a mercaptan with thiophosgene in an aprotic solvent such as chloroform at −5° to +10° C. as described in Example 2. Alternatively, the compounds (1) can be prepared by mixing a mercaptan with dichloromethanesulfenyl chloride in a suitable solvent such as dichloromethane at −5° to +10° C.

The following examples and Table 1 illustrate the preparation of compounds of this invention. Unless otherwise indicated, all parts are by weight and all temperatures are in °C.

EXAMPLE 1

2-(Cyclohexylthio) [1,2,4]dithiazolo-[1,5-b] [1,2,4]-dithiazole-4-$S^{IV}$

To a solution of 8.1 g (0.1 mole) of dry sodium thiocyanate in 120 ml. of acetonitrile was added dropwise with stirring, 11.5 g (0.05 mole) of cyclohexyl dichloromethyl disulfide, prepared as described in Example 2. After the mixture was heated under reflux for two hours, the insoluble material was filtered off, and the filtrate was evaporated to give an orange solid. This material was recrystallized from ethanol to give 2.5 g of orange crystals of 2-(cyclohexylthio) [1,2,4]-dithiazolo-[1,5-b] [1,2,4]-dithiazole-4-$S^{IV}$, m.p. 109°–113° C. Examples of compounds which can be prepared by this method are listed in Table 1.

EXAMPLE 2

Cyclohexyl Dichloromethyl Disulfide

To a solution of 20.0 g (0.17 mole) of thiophosgene in 100 ml. of chloroform cooled to 0° C. was added dropwise with stirring 20.2 g (0.17 mole) of cyclohexyl mercaptan. To this mixture was added dropwise a solution of 2.5 g of sodium hydroxide in 25 ml. of water at such a rate as to keep the temperature less than 8° C. When the addition was complete, the chloroform layer was separated and dried over calcium chloride. The solvent was evaporated, and the residue was distilled under reduced pressure to give 26.4 g of yellow cyclohexyl dichloromethyl disulfide, b.p. 118°–125° C. (5 Torr.)

TABLE 1

2-Alkylthio-[1,2,4]-dithiazolo-[1,5-b][1,2,4]-dithiazoles-4-$S^{IV}$

| R | m.p., °C. |
|---|---|
| $CH_3$ | 108–109 |
| $C_2H_5$ | 111–112 |
| n-$C_3H_7$ | 117–118 |
| i-$C_3H_7$ | 116–120 |
| n-$C_4H_9$ | 96–97 |
| i-$C_4H_9$ | 100–102 |
| i-$C_5H_{11}$ | 89–90 |
| n-$C_6H_{13}$ | 87–88 |
| n-$C_{10}H_{21}$ | |
| $ClCH_2CH_2CH_2$— | |
| $CH_2$=$CHCH_2$— | |
| $CH_2$=$C(CH_3)$—$CH_2$— | 73–77 |
| $CH_3(CH_2)_4CH$=$CHCH_2$— | |
| $CH_2$=$C(Cl)$—$CH_2$— | |
| cyclopropyl-H | |
| cyclopentyl-H | 123–126 |
| cyclohexyl-H | 109–113 |
| cycloheptyl-H | |
| cyclopentyl-$CH_2$— (H) | |
| cyclohexyl-$CH_2$— (H) | |
| phenyl-$CH_2$— | 119–121 |
| phenyl-$CH_2CH_2$— | 97–100 |
| phenyl-$CH_2CH_2CH_2$— | 90–91 |
| $CH_3$-phenyl-$CH_2$— | |

TABLE 1-continued

2-Alkylthio-[1,2,4]-dithiazolo-
[1,5-b][1,2,4]-dithiazoles-4-S$^{IV}$

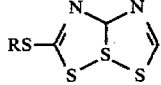

| R | m.p., °C. |
|---|---|
| CH$_3$O–C$_6$H$_4$–CH$_2$– | |
| O$_2$N–C$_6$H$_4$–CH$_2$– | |
| o-F–C$_6$H$_4$–CH$_2$– | 111–114 |
| Cl–C$_6$H$_4$–CH$_2$– | 98–100 |
| 2,4-Cl$_2$–C$_6$H$_3$–CH$_2$– | |
| Br–C$_6$H$_4$–CH$_2$– | |

Utility

The compounds of this invention are useful in protecting growing plants, fresh fruits and vegetables, grains in storage and a number of other plant or animal products such as fabric, wood, hides and tallow from fungus diseases. Certain petroleum products can be protected, and even fungus diseases which affect warm-blooded animals, including man, can be reduced or completely controlled with the compounds of this invention.

With respect to plant fungus diseases, the compounds of this invention are effective on a variety of host plants with a margin of plant safety. These diseases can be incited by fungal pathogens represented by, but not limited to, *Venturia inaequalis, Phytophthora infestans, Plasmopara viticola, Uromyces phaseoli* ver. typica, *Pyricularia oryzae, Botrytis cinerea, Cercospora beticola,* and *Erysiphe cichoracearum.*

Disease control can be accomplished by applying the compounds of this invention to the portion of the plant to be protected. The compounds may be applied as a preventive treatment prior to inoculation with the pathogen.

Rates of application for compounds of this invention will be influenced by specific host plants, fungal pathogens, and many factors of the environment and, therefore, exact rates are usually determined for the particular use conditions. Foliage sprayed with concentrations ranging from 1 to about 500 ppm active ingredient, however, is usually protected from disease under normal conditions.

Compositions of this invention may contain, in addition to the compounds of this invention, conventional pesticides, such as insecticides, miticides, bactericides, nematocides, fungicides, or other agricultural chemicals such as growth modifying agents, fertilizer ingredients, and the like. The proper choice of conventional pesticides and their amounts can be made by one skilled in the art of protecting plants from pest depradations.

The following are illustrative of the agricultural chemicals that may be included in compositions or added to sprays containing one or more of the active compounds of this invention:

bis(dimethylthiocarbamoyl)disulfide; or tetramethylthiuram disulfide (thiram);

metal salts of ethylenebisdithiocarbamic acid or propylenebisdithiocarbamic acids, e.g. manganese, zinc, iron and sodium salts (maneb or zineb);

n-dodecylguanidine acetate (dodine);

N-(trichloromethylthio)phthalimide (folpet);

N-[(trichloromethyl)thio]-4-cyclohexene-1,2-dicarboximide (captan);

cis-N-[(1,1,2,2-tetrachloroethyl)thio]-4-cyclohexene-1,2-dicarboximide (captafol);

2,4-dichloro-6-(o-chloroanilino)-α-triazine ("Dyrene");

a coordination product of zinc ion and manganese ethylenebisdithiocarbamate (mancozeb);

3,3'-ethylenebis(tetrahydro-4,6-dimethyl-2H-1,3,5-thiadiazine-2-thione), (milneb);

triphenyltin hydroxide (fentin hydroxide);

triphenyltin acetate (fentin acetate);

N'-dichlorofluoromethylthio-N,N-dimethyl-N'-phenylsulfamide (dichlorofluanid); tetrachloroisophthalonitrile (chlorothalonil);

tribasic copper sulfate;

fixed copper;

sulfur;

methyl 1-(butylcarbamoyl)-2-benzimidazolecarbamate (benomyl);

methyl 2-benzimidazolecarbamate;

1,2-bis(3-methoxycarbonyl-2-thioureido)benzene (methyl thiophanate);

2-cyano-N-(ethylcarbamoyl)-2-methoxyiminoacetamide.

methyl D,L-N-(2,6-dimethylphenyl)-N-(2'-methoxyacetyl)alaninate (Ridomil ®)

2,6-dichloro-4-nitrobenzenamine (Dicloran)

The agricultural chemicals listed above are merely exemplary of compounds that may be mixed with the active compounds of this invention to broaden the spectrum of disease control.

In the following examples of biological activity for the compounds of this invention percent disease control was calculated by the formula $$100 - \left[ \frac{\text{disease rating on treated}}{\text{disease rating on untreated}} \times 100 \right] = \text{percent control}$$

Little or no plant injury was noted when host plants specified in the following examples were treated with compounds of this invention at the specified application rates.

EXAMPLE 3

Compounds of this invention were dissolved in acetone in an amount equal to 10% of the final volume and then suspended at a concentration of 80 ppm in purified water containing 250 ppm of the surfactant Trem ® 014 (polyhydric alcohol esters). This suspension was sprayed to the point of run-off on seedling apple plants growing in pots and trained to a single shoot. The following day, the apple seedlings were inoculated with a spore suspension of the fungus *Venturia inaequalis* (Apple Scab) and incubated in a saturated humidity chamber at 20° C. for 24 hours, and then in a greenhouse for an additional eleven days. Disease ratings were made of two susceptible leaves on each of four replicate plants for each treatment. As shown in Table 2, treated plants were completely free of or had only a few foliar lesions in contrast to untreated plants which were covered with scab lesions.

TABLE 2

| Compound | Percent Apple Scab Control |
|---|---|
| 2-[(1-Methylethyl)thio] [1,2,4]-dithiazolo-[1,5-b] [1,2,4]-dithiazole-4-$S^{IV}$ | 100 |
| 2-(Ethylthio) [1,2,4]-dithiazolo-[1,5-b] [1,2,4]-dithiazole-4-$S^{IV}$ | 99 |
| 2-[(Phenylmethyl)thio] [1,2,4]-dithiazolo-[1,5-b] [1,2,4]-dithiazole-4-$S^{IV}$ | 94 |
| 2-(Cyclohexylthio) [1,2,4]-dithiazolo-[1,5-b] [1,2,4]-dithiazole-4-$S^{IV}$ | 99 |
| 2-[(Phenylethyl) thio] [1,2,4]-dithiazolo-[1,5-b] [1,2,4]-dithiazole-4-$S^{IV}$ | 97 |
| 2-(Cyclopentylthio) [1,2,4]-dithiazolo-[1,5-b] [1,2,4]-dithiazole-4-$S^{IV}$ | 100 |
| 2-[(2-Methyl-2-propenyl) thio] [1,2,4]-dithiazolo-[1,5-b] [1,2,4]-dithiazole-4-$S^{IV}$ | 100 |
| 2-(Propylthio) [1,2,4]dithiazolo-[1,5-b] [1,2,4]-dithiazole-4-$S^{IV}$ | 100 |
| 2-(Butylthio) [1,2,4]dithiazolo-[1,5-b] [1,2,4]dithiazole-4-$S^{IV}$ | 100 |
| 2-(3-Methylbutylthio) [1,2,4]-dithiazolo-[1,5-b] [1,2,4]-dithiazole-4-$S^{IV}$ | 100 |
| 2-(2-Methylpropylthio) [1,2,4]-dithiazolo-[1,5-b] [1,2,4]-dithiazole-4-$S^{IV}$ | 100 |
| 2-(3-Phenylpropylthio) [1,2,4]-dithiazolo-[1,5-b] [1,2,4]-dithiazole-4-$S^{IV}$ | 87 |
| 2-[(4-Chlorophenylmethyl)thio]-[1,2,4]-dithiazolo-[1,5-b]-[1,2,4]-dithiazole-4-$S^{IV}$ | 96 |

EXAMPLE 4

Compounds of this invention were dissolved in acetone in an amount equal to 10% of the final volume and then suspended at a concentration of 80 ppm in purified water containing 250 ppm of the surfactant, Trem ® 014 (polyhydric alcohol esters). This suspension was sprayed to the point of run-off on five week old Bonnie Best tomato plants growing in the greenhouse. The next day the plants were inoculated with a spore suspension of the fungus, *Phytophthora infestans* (Tomato Late Blight) which was derived from tomato plants previously inoculated with the pathogen. The chemically-sprayed and inoculated tomato plants were incubated in a saturated humidity at 20° C. for 24 hours and then in the greenhouse an additional three days before being rated. Results are shown in Table 3.

TABLE 3

| Compound | Percent Tomato Late Blight |
|---|---|
| 2-[(1-Methylethyl)thio] [1,2,4]-dithiazolo[1,5-b] [1,2,4]-dithiazole-4-$S^{IV}$ | 87 (2B)[1] |
| 2-(Ethylthio) [1,2,4]-dithiazolo-[1,5-b] [1,2,4]-dithiazole-4-$S^{IV}$ | 95 (2B) |
| 2-(Cyclohexylthio) [1,2,4]-dithiazolo-[1,5-b] [1,2,4]-dithiazole-4-$S^{IV}$ | 83 (2B) |

TABLE 3-continued

| Compound | Percent Tomato Late Blight |
|---|---|
| 2-(Propylthio) [1,2,4]dithiazolo-[1,5-b] [1,2,4]dithiazole-4-$S^{IV}$ | 95 (2B) |

[1]The codes in parentheses are phytotoxicity ratings on a 0 to 10 scale where 0 = no injury and 10 = complete kill.
B designates leaf burn.

EXAMPLE 5

Compounds of this invention were dissolved in acetone in an amount equal to 10% of the final volume and suspended in purified water with 0.001% Trem ® 014 (polyhydric alcohol ester) surfactant.

For preventive tests, compounds of this invention were applied to grape plants at a concentration of 80 ppm 24 hours prior to inoculation with the pathogen.

Sporongia of the fungal pathogen *Plasmopara viticola* (Grape Downy Mildew) were collected from previously infected grape leaves and sprayed on the test plants. The treated and inoculated grape plants were incubated in a saturated humidity chamber at 20° C. for 48 hours, placed on a greenhouse bench for 5 days and reincubated for 48 hours before disease control evaluations were made. Results are shown in Table 4.

TABLE 4

| Compound | Percent Grape Downy Mildew Control |
|---|---|
| 2-[ 1-Methylethyl)thio] [1,2,4]-dithiazolo[1,5-b] [1,2,4]-dithiazole-4-$S^{IV}$ | 100 (2C)[1] |
| 2-[(Phenylmethyl)thio] [1,2,4] dithiazolo-[1,5-b] [1,2,4]-dithiazole-4-$S^{IV}$ | 87 |
| 2-(Hexylthio)-[1,2,4]-dithiazolo-[1,5-b] [1,2,4]-dithiazole-4-$S^{IV}$ | 96 |

[1]The code in parentheses are phytotoxicity ratings on a 0 to 10 scale where 0 = no injury and 10 = complete kill. C indicates chlorosis

EXAMPLE 6

Compounds of this invention were dissolved in acetone in an amount equal to 10% of the final volume and then suspended at a concentration of 80 ppm in purified water containing 250 ppm of the surfactant Trem ® 014 (polyhydric alcohol esters). This suspension was sprayed to the point of run-off on 10-day old greenhouse grown Pinto beans with the first set of tree leaves expanded. The next day the plants were inoculated with a spore suspension of the fungus, *Uromyces phaseoli* var. *typica* (Bean Rust). The inoculated bean plants were incubated in a saturated humidity chamber at 20° C. for 24 hours, and then in the greenhouse for an additional week. Disease ratings were made by counting the number of lesions on the two primary leaves of three replicate plants for each treatment. Results are shown in Table 5.

TABLE 5

| Compound | Percent Bean Rust Control |
|---|---|
| 2-[ (1-Methylethyl)thio] [1,2,4]-dithiazolo[1,5-b] [1,2,4]-dithiazole-4-$S^{IV}$ | 98 |
| 2-(Ethylthio) [1,2,4]-dithiazolo-[1,5-b] [1,2,4]-dithiazole-4-$S^{IV}$ | 100 |
| 2-(propylthio) [1,2,4]-dithiazolo- | 99 |

TABLE 5-continued

| Compound | Percent Bean Rust Control |
|---|---|
| [1,5-b] [1,2,4]dithiazole-4-S$^{IV}$ | |

EXAMPLE 7

Compounds of this invention were dissolved in acetone in an amount equal to 10% of the final volume and suspended in purified water with 0.001% Trem ® 014 (polyhydric alcohol ester) surfactant.

For preventive tests, compounds of this invention were applied to rice plants at a concentration of 80 ppm 24 hours prior to inoculation with the pathogen. Spores of the fungal pathogen *Pyricularia oryzae* (Rice Blast) were collected from agar plates previously seeded with the fungus and then sprayed on the test plants. The treated and inoculated seedling rice plants were incubated in a saturated humidity chamber at 24° C. for 24 hours and placed in a greenhouse bench for 9 days after which disease control was evaluated. Results are shown in Table 6.

TABLE 6

| Compound | Percent Rice Blast Control |
|---|---|
| 2-[(Phenylmethyl)thio] [1,2,4]-dithiazolo-[1,5-b] [1,2,4]-dithiazole-4-S$^{IV}$ | 68 |
| 2-(Cyclohexylthio) [1,2,4]-dithiazolo-[1,5-b] [1,2,4]-dithiazole-4-S$^{IV}$ | 93 |
| 2-[(Phenylethyl)thio] [1,2,4]-dithiazolo-[1,5-b] [1,2,4]-dithiazole-4-S$^{IV}$ | 88 |
| 2-[(4-Chlorophenylmethyl)thio]-[1,2,4]-dithiazolo-[1,5-b]-[1,2,4]-dithiazole-4-S$^{IV}$ | 96 |

EXAMPLE 8

Compounds of this invention were dissolved in acetone in an amount equal to 10% of the final volume and then suspended at concentrations of 80 ppm or 16 ppm in purified water containing 250 ppm of the surfactant Trem ® 014. The suspensions were sprayed to the point of run-off on 2-week old broadbean plants. The following day the plants were inoculated with a spore suspension of the fungus *Botrytis cinerea* and incubated in a transparent, saturated humidity chamber for 72 hours. After 2 days additional incubation in the greenhouse, disease ratings were made. Table 7 shows the minimum effective concentrations for control of *Botrytis cinerea* with compounds of this invention.

TABLE 7

| Compound | Percent *Botrytis cinerea* Control | |
|---|---|---|
| | 80 ppm | 16 ppm |
| 2-[(1-Methylethyl)thio] [1,2,4]-dithiazolo[1,5-b] [1,2,4]-dithiazole-4-S$^{IV}$ | — | 87 (2B)[1] |
| 2-(Cyclohexylthio) [1,2,4]-dithiazolo-[1,5-b] [1,2,4]-dithiazole-4-S$^{IV}$ | 88 (3B)[1] | — |
| 2-(Cyclopentylthio) [1,2,4]-dithiazolo-[1,5-b] [1,2,4]-dithiazole-4-S$^{IV}$ | .97 (3B)[1] | — |

TABLE 7-continued

| Compound | Percent *Botrytis cinerea* Control | |
|---|---|---|
| | 80 ppm | 16 ppm |
| dithiazole-4-S$^{IV}$ | | |

[1]The codes in parenthesis are phytotoxicity ratings on a 0 to 10 scale where 0 = no injury and 10 = complete kill.
B designates burn.

EXAMPLE 9

Compounds of this invention were dissolved in acetone in an amount equal to 10% of the final volume and then suspended at a concentration of 80 ppm in purified water containing 250 ppm of the surfactant Trem ® 014 (polyhydric alcohol esters). This suspension was sprayed to the point of run-off on 6-week old sugar beet seedlings. The following day the seedlings were inoculated with a spore suspension of the fungus *Cercospora beticola* (Cercospora Leaf Spot) and incubated in a transparent, saturated humidity chamber for 72 hours. After 11 to 15 days additional incubation in a greenhouse, disease ratings were made. As shown in Table 8, compounds of this invention are effective for control of *Cercospora beticola*.

TABLE 8

| Compound | Percent Cercospora beticola Control |
|---|---|
| 2-[(1-Methylethyl)thio] [1,2,4]-dithiazolo[1,5-b] [1,2,4]-dithiazole-4-S$^{IV}$ | 94 (2B,1H)[1] |
| 2-(Cyclohexylthio) [1,2,4]-dithiazolo-[1,5-b] [1,2,4]-dithiazole-4-S$^{IV}$ | 64 |
| 2-(Cyclopentylthio) [1,2,4]-dithiazolo-[1,5-b] [1,2,4]-dithiazole-4-S$^{IV}$ | 83 (2B) |

[1]The codes in parenthesis are phytotoxicity ratings on a 0 to 10 scale where 0 = no injury and 10 = complete kill. B designates burn and H designates malformation due to cupping of the leaves.

EXAMPLE 10

Compounds of this invention were dissolved in acetone in an amount equal to 10% of the final volume and then suspended at a concentration of 80 ppm in purified water containing 250 ppm of the surfactant Trem ® 014 (polyhydric alcohol esters). This suspension was sprayed to the point of run-off on 2-week old Straight Eight variety cucumber plants. The following day the plants were inoculated with a spore suspension of the fungus *Erysiphe cichoracearum* (Cucumber Powdery Mildew) and incubated in a greenhouse for 8-days when disease ratings were made. As shown in Table 9, most compounds tested provided disease control with little or no phytotoxicity, as treated plants had only a few foliar lesions in contrast to untreated plants which were covered with powdery mildew.

TABLE 9

| Compound | Percent Cucumber Powdery Mildew Control |
|---|---|
| 2-[(1-Methylethyl)thio][1,2,4]-dithiazolo[1,5-b][1,2,4]-dithiazole-4-S$^{IV}$ | 99 (1H)[1] |
| 2-(Ethylthio)[1,2,4]-dithiazolo-[1,5-b][1,2,4]-dithiazole-4-S$^{IV}$ | 100 (1H) |
| 2-[(Phenylmethyl)thio][1,2,4]-dithiazolo-[1,5-b][1,2,4]-di-thiazole-4-S$^{IV}$ | 20 |

TABLE 9-continued

| Compound | Percent Cucumber Powdery Mildew Control |
|---|---|
| 2-(Cyclohexylthio)[1,2,4]-dithiazolo-[1,5-b][1,2,4]-dithiazole-4-$S^{IV}$ | 83 |
| 2-[(Phenylethyl)thio][1,2,4]-dithiazolo-[1,5-b][1,2,4]-dithiazole-4-$S^{IV}$ | 20 |
| 2-(Cyclopentylthio)[1,2,4]-dithiazolo-[1,5-b][1,2,4]-dithiazole-4-$S^{IV}$ | 92 (2H) |
| [(2-Methyl-2-propenyl)thio]-[1,2,4]-dithiazolo-[1,5-b]-[1,2,4]-dithiazole-4-$S^{IV}$ | 9 (1H) |
| 2-(Propylthio)[1,2,4]-dithiazolo-[1,5,-b][1,2,4]-dithiazole-4-$S^{IV}$ | 100 (2H) |
| 2-(Butylthio)[1,2,4]-dithiazolo-[1,5-b][1,2,4]-dithiazole-4-$S^{IV}$ | 99 (2H) |
| 2-(3-Methylbutylthio)[1,2,4]-dithiazolo-[1,5-b][1,2,4]-dithiazole-4-$S^{IV}$ | 99 |

[1]The codes in parenthesis are phytotoxicity ratings on a 0 to 10 scale where 0 = no injury and 10 = complete kill. H designates malformation due to cupping of the leaves.

EXAMPLE 11

A compound of this invention was dissolved in acetone in an amount equal to 10% of the final volume and suspended in purified water with 0.001% Trem ® 014 (polyhydric alcohol ester) surfactant.

For preventive tests, the compound was applied to wheat plants at a concentration of 80 ppm 24 hours prior to inoculation with the pathogen. Spores of the fungal pathogen *Puccinia graminis* (Wheat Rust) were collected from previously infected wheat plants and sprayed on to test plants. The treated and inoculated plants were incubated in a saturated humidity chamber at 20° C. for 24 hours, placed on a greenhouse bench for 10 days after which disease ratings were made. Results are shown below.

TABLE 10

| Compound | Percent Wheat Rust Control |
|---|---|
| 2-[(Phenylethyl)thio][1,2,4]-dithiazolo-[1,5-b][1,2,4]-dithiazole-4-$S^{IV}$ | 37 |

In addition to their usefulness in protecting growing plants as described above, the compounds and methods of this invention have utility in many other applications. Fruits, tubers, bulbs, roots, seeds and other plant parts harvested for food, animal feed or for other purposes can be protected from fungus deterioration during processing, distribution and storage. Seeds, tubers, cuttings and other plant propagation materials can be protected from fungus attack during handling and storage as well as in the soil after planting. Wood, fabric, fiber board, paper and other industrial materials can be protected from unsightly stain and destructive decay caused by fungi. Luggage, shoes, shower curtains, carpets, mats, clothing and other useful household or public items can be protected from rot, fungus stains and surface mold growth. Painted surfaces can be protected from stain and discoloration by the incorporation of a compound of this invention into the paint formulation.

The following examples illustrate the activity of the compounds of this invention in additional applications. All proportions or rates stated are by weight unless otherwise indicated.

EXAMPLE 2

A compound of this invention, 2-[(1-methylethyl)thio][1,2,4]-dithiazolo-[1,5-b][1,2,4]-dithiazole-4-$S^{IV}$, was dissolved in acetone. This solution was then added to a molten sterile malt agar growth medium in an amount to provide 100 ppm of the fungicidal compound. The agar containing the 100 ppm of this invention was then poured into sterile culture plates and allowed to solidify. The plates were then inoculated with a number of the fungi commonly associated with post-harvest deterioration and other types of fungus damage. The following fungus genera were controlled totally or in part: Botrytis, Monilinia, Phytophthora, Fusarium, Verticillium Thielaviopsis and Penicillium. This clearly demonstrates the broad spectrum of fungi controlled by the compounds and methods of this invention.

EXAMPLE 13

An aqueous suspension concentrate was prepared as follows:

| | |
|---|---|
| 2-[(1-Methylethyl)thio][1,2,4]-dithio-[1,5-b]-[1,2,4]-dithiazole-4-$S^{IV}$ | 30.00% |
| Polyacrylic acid, sodium salt | 0.35% |
| Low viscosity polyvinyl alcohol | 1.50% |
| Water | 68.15% |

The active compound was ground to pass a 30 mesh screen and then mixed with the remaining formulation ingredients and sand ground to a particle size below 5 microns.

Green pine lumber coming from the saw in a mill was dipped for two minutes in a bath containing a suspension of the formulation prepared as described above. The amount of suspension concentrate used was such as to provide 4000 parts per million of the active compound in the bath. Similar lumber was not dipped. All of the lumber was piled together in a seasoning yard. After three months, the lumber was examined. The lumber that had been dip-treated was all bright and clean. The unprotected lumber was heavily covered with green mold (Penicillium spp.) and stained by *Ceratostomella pilifera.*

EXAMPLE 14

A dust concentration was prepared as follows:

| | |
|---|---|
| 2-[(1-Methylethyl)thio][1,2,4]-dithiazolo-[1,5-b][1,2,4]-dithiazole-4-$S^{IV}$ | 80% |
| Synthetic fine silica | 20% |

The above ingredients were blended and milled to a particle size below 10 microns, followed by reblending.

Two experimental lots of house paint were prepared in a similar manner except that 0.5% by weight of the active compound of this formulation was milled with the dry ingredients in one lot, whereas none of the concentrate was added to the other lot. Test boards were painted with each lot. After one year exposure in Florida, the board with the paint to which the concentrate was not added was badly stained by fungus growth including species of Penicillium and other genera. The board with the paint containing the compound of this invention remained bright.

EXAMPLE 15

| | |
|---|---|
| 2-[(1-Methylethyl)thio][1,2,4]-dithiazolo-[1,5-b][1,2,4]-dithiazole-4-S$^{IV}$ | 15% |
| Pyrophyllite | 85% |

The active ingredient and an equal amount of pyrophyllite was first blended and micropulverized to a particle size smaller than 100 microns, then reblended with the remainder of the diluent.

Sugar cane seed pieces cut in November were divided into eight lots. Four of these lots were dusted in such a way as to cover all surfaces with the dust prepared as described above. The other four lots were dusted with the inert diluent only. All lots were stored under similar conditions until the following February at which time they were examined. The four lots that had been treated with the compound of this invention were in good condition. The four unprotected lots, on the contrary, were so badly rotted by fungi of the genus Fusarium that they could not be planted.

EXAMPLE 16

An aqueous suspension concentrate was prepared as follows:

| | |
|---|---|
| 2-[(1-Methylethyl)thio][1,2,4]-dithiazolo-[1,5-b][1,2,4]-dithiazole-4-S$^{IV}$ | 30.00% |
| Polyacrylic acid, sodium salt | 0.35% |
| Low viscosity polyvinyl alcohol | 1.50% |
| Water | 68.15% |

The active component was ground to pass a 30 mesh screen and was then mixed with the remaining formulation ingredients and sand ground to a particle size below 5 microns.

Six field crates of oranges were picked from a commercial grove in Florida. Three of these crates of oranges were dipped for 3 minutes in a water bath containing a suspension made from the above formulation, in an amount to give 300 parts per million by weight of the active ingredient of this invention. A polyethylene glycol ester of oleic acid surface active agent was present at the rate of 150 ppm of total liquid. The remaining three crates were dipped in a similar fashion in water with the surface active agent only. All crates were set aside in a citrus storage house for three weeks. At the end of this time, all fruit were examined. The fruit that had been dip-treated with the compound of this invention was still in good condition, but the fruit that was not so protected was largely rotted by the blue mold fungus (*Penicillium digitatum*).

The compounds of this invention are also useful for control of exthropod pests and are particularly active on white fly, Trialeurodes spp; mosquito larvae, hedes, Anopheles and Clux spp; and mites, Tetranychos urticae, Panonychus ulmi, etc. They may be applied as aqueous dispersion by conventional methods ordinarily to the pests themselves or to the locus of anthropod infestation. As used herein in the claims, the term "locus of infestation" shall mean that the compounds of this invention, when used to control insects and larval pests, may be applied directly to the pests themselves, an area of pest infestation or to an area likely to be infested. The quantity of active ingredient needed for control will depend on many factors such as intensity of the infestation, the particular species involved, frequency and amount of rainfall, temperature and others. Generally, from 0.05 to 5 kg/ha are sufficient to give commercially acceptable exthropod control. Preferred for reasons of economy and effectiveness are rates of from 0.1 to 1.0 kg/ha.

In addition, the compounds of this invention may be used in combination with the following insecticides, nematicides and acaricides for a broader spectrum of pest control.

Insecticides 3-hydroxy-N-methylcrotonamide(dimethylphosphate)ester (Azodrin ®)

methylcarbamic acid, ester with 2,3-dihydro-2,2-dimethyl-7-benzofuranol (Furadan ®)

O-[2,4,5-trichloro-α-(chloromethyl)benzyl]phosphoric acid, O',O'-dimethyl ester (Gardona ®)

2-mercaptosuccinic acid, diethyl ester, S-ester with thionophosphoric acid, dimethyl ester (Malathion ®) phosphorothioic acid, O,O-dimethyl, O-p-nitrophenyl ester (methyl parathion)

methylcarbamic acid, ester with α-naphthol (Sevin ®)

methyl O-(methylcarbamoyl)thiolacetohydroxamate (methomyl)

O,O-diethyl-O-(2-isopropyl-4-methyl-6-pyrimidyl-phosphorothioate (Diazinon ®)

octachlorocamphene (toxaphene)

O-ethyl O-p-nitrophenyl phenylphosphonothioate (EPN) cyano(3-phenoxyphenyl)-methyl-4-chloro-α-(1-methylethyl)benzeneacetate (Pydrin ®)

(3-phenoxyphenyl)methyl(+)-cis,trans-3-(2,2-dichloroethenyl)-2,2-dimethylcyclopropanecarboxylate (Ambush ®)

O-ethyl-S-(p-chlorophenyl)ethylphosphonodithioate (Curacron ®)

phosphorothiolothionic acid, O-ethyl-O-[4-(methylthio)-phenyl]-S-n-propyl ester (Bolstar ®)

Nematicides

S-methyl 1-(dimethylcarbamoyl)-N-(methylcarbamoyloxy)-thioformimidate (Vydate ®)

S-methyl 1-carbamoyl-N-(methylcarbamoyloxy)thioformimidate

N-isopropylphosphoramidic acid, O-ethyl-O'-[4-(methylthio)-m-tolyl]diester (Nemacur ®)

Acaricides senecioic acid, ester with 2-sec-butyl-4,6-dinitrophenol (Morocide ®)

6-methyl-1,3-dithiolo[2,3-β]quinonolin-2-one (Morestan ®) ethyl 4,4'-dichlorobenzilate (Chlorobenzilate ®)

1,1-bis(p-chlorophenyl)-2,2,2-trichloroethane (Kelthane ®)

bis(pentachloro-2,4-cyclopentadien-lyl) (Pentac ®)

tricyclohexyl trihydroxide (Plictran ®)

EXAMPLE 17

Summer squash plants 18–26 cm in height, planted 3 per 15 cm pots, and having a severe matinal infestation of greenhouse white fly were sprayed to run-off with dispersions of 2-[(1-methylethyl)thio]-[1,2,4]-dithiazolo[1,5-b][1,2,4]-dithiazole-4-S$^{IV}$ (I). Six replicates were used per treatment and for the untreated control. Evaluations were made 1 and 6 days after application and are set forth below.

| Treatment | Spray Concentration (ppm) | % Control 1 Day | 6 Days |
|---|---|---|---|
| (I) | 300 | 88 | 91 |
|  | 100 | 71 | 80 |
| Untreated Control | — | 0(191)[1] | 0(288)[1] |

[1]Total number of white flies present.

EXAMPLE 18

Groups of 25 newly hatched yellow fever mosquito larvae were placed in 25 ml aliquots of water. Weighed portions of each of the compounds listed below were dissolved in acetone, and predetermined quantities of these solutions were added individually to the jars containing the mosquito larvae. Food for the larvae was added periodically. The jars were examined daily and dead larvae and pupae were noted. Results were recorded when adults had emerged and the remaining larvae or pupae were dead. A dose response curve was prepared for each compound and the $EC_{50}$ (concentration required to kill 50% of the mosquito larvae or pupae) expressed in ppm was estimated. Data are presented below:

| Test Compound | Evaluation $EC_{50}$ ppm |
|---|---|
| 2-[(1-methylethyl)thio][1,2,4]-dithiazolo[1,5-b][1,2,4]-dithiazole-4-$S^{IV}$ | 0.20 |
| 2-(n-hexylthio)[1,2,4]-dithiazolo-[1,5-b][1,2,4]-dithiazole-4-$S^{IV}$ | 0.096 |
| [(phenylmethyl)thio][1,2,4]-dithiazolo-[1,5-b][1,2,4]-dithiazole-4-$S^{IV}$ | 0.058 |
| 2-(cyclohexylthio)[1,2,4]-dithiazolo-[1,5-b][1,2,4]-dithiazole-4-$S^{IV}$ | 0.108 |
| 2-[(phenylethyl)thio][1,2,4]-dithiazolo-[1,5-b][1,2,4]-dithiazole-4-$S^{IV}$ | 0.084 |
| 2-(4-chlorophenylmethylthio)[1,2,4]-dithiazolo-[1,5-b][1,2,4]-dithiazole-4-$S^{IV}$ | 0.064 |

EXAMPLE 19

Test units consisted of plant pots containing two red kidney bean plants in the two-leaf stage per pot. The plants were infested with two-spotted mites and sprayed to run-off with solutions of the compounds of this invention. Solutions were made by dissolving weighed quantities of the active ingredients in 10 ml of acetone and then diluting to volume with water containing 1:3000 of Surfactant F. Mortality was evaluated two days after spraying.

| Test Compound | % Control of Mites At 2000 ppm |
|---|---|
| 2-[(1-methylethyl)thio][1,2,4]-dithiazolo[1,5-b][1,2,4]-dithiazole-4-$S^{IV}$ | 100 |
| 2-(n-hexylthio)[1,2,4]-dithiazolo-[1,5-b][1,2,4]-dithiazole-4-$S^{IV}$ | 100 |

Formulation

Useful formulations of the compounds of Formulas I and II can be prepared in conventional ways. They include dusts, granules, pellets, solutions, wettable powders, and the like. Many of these may be applied directly to the plant. Sprayable formulations can be extended in suitable media and used at spray volumes of from a few pints to several hundred gallons per acre. High strength compositions are primarily used as intermediates for further formulations. The formulations can contain from about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

|  | Active Ingredient | Inert Diluent(s) | Surfactant(s) |
|---|---|---|---|
| Wettable Powders | 20–90 | 0–74 | 1–10 |
| Oil Suspensions, Solutions | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. McCutcheon's "Detergents and Emulsifiers Annual", MC Publishing Co., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions can be prepared by simply mixing the ingredients. Fine solid compositions can be made by blending and, usually, grinding as in a hammer or fluid energy mill. Suspensions can be prepared by wet milling. Granules and pellets may be made by spraying the active material upon preformed granular carriers or by known agglomeration techniques.

Typical formulations are illustrated in the following examples.

EXAMPLE 20

| Wettable Powder |  |
|---|---|
| 2-[(1-Methylethyl)thio][1,2,4]-dithiazolo-[1,5-b]-[1,2,4]-dithiazole-4-$S^{IV}$ | 30% |
| Dioctyl sodium sulfosuccinate | 1.5% |
| Sodium ligninsulfonate | 3% |
| Low viscosity methyl cellulose | 1.5% |
| Attapulgite | 64% |

The ingredients are thoroughly blended, passed through an air mill to produce an average particle size under 15 microns, reblended, and sifted through a U.S.S. No. 50 sieve (0.3 mm opening) before packaging.

All compounds of this invention may be formulated in the same manner.

EXAMPLE 21

| Wettable Powder | |
| --- | --- |
| 2-(Ethylthio)[1,2,4]-dithiazolo-[1,5-b][1,2,4]-dithiazole-4-$S^{IV}$ | 50% |
| Sodium alkylnaphthalenesulfonate | 2% |
| Low viscosity methyl cellulose | 2% |
| Diatomaceous earth | 46% |

The ingredients are blended, coarsely hammer-milled and then air milled to produce particles of active ingredient practically all below about 10 microns in diameter. The product is reblended before packaging.

EXAMPLE 22

| Dust | |
| --- | --- |
| Wettable Powder of Example 21 | 10% |
| Pyrophyllite (powder) | 90% |

The wettable powder and the pyrophyllite diluent are throughly blended and then packaged. The product is suitable for use as a dust.

EXAMPLE 23

| Solution | |
| --- | --- |
| 2-[(Phenylmethyl)thio][1,2,4]-dithiazolo-[1,5-b]-[1,2,4]-dithiazole-4-$S^{IV}$ | 30% |
| Dimethylformamide | 70% |

The ingredients are combined and stirred to produce a solution which can be used for low volume applications.

EXAMPLE 24

| Granule | |
| --- | --- |
| Wettable Powder of Example 20 | 15% |
| Gypsum | 69% |
| Potassium sulfate | 16% |

The ingredients are blended in a rotating mixer and water sprayed on to accomplish granulation. When most of the material has reached the desired range of 1.0 to 0.42 mm. (U.S.S. No. 18 to 40 sieves), the granules are removed, dried, and screened. Oversize material is crushed to produce additional material in the desired range. These granules contain 4.5% active ingredient.

EXAMPLE 25

| Extruded Pellet | |
| --- | --- |
| 2-(Cylcohexylthio)[1,2,4]-dithiazolo-[1,5-b][1,2,4]-dithiazole-4-$S^{IV}$ | 25% |
| Anhydrous sodium sulfate | 10% |
| Crude calcium ligninsulfonate | 5% |
| Sodium alkylnaphthalenesulfonate | 1% |
| Calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm opening). The granules held on a U.S.S. No. 40 sieve (0.42 mm opening) may be packaged for use and the fines recycled.

EXAMPLE 26

| Aqueous Suspension | |
| --- | --- |
| 2-[(Phenylethyl)thio][1,2,4]-dithiazolo-[1,5-b]-[1,2,4]-dithiazole-4-$S^{IV}$ | 25% |
| Hydrated attapulgite | 3% |
| Crude calcium ligninsulfonate | 10% |
| Sodium dihydrogen phosphate | 0.5% |
| Water | 61.5% |

The ingredients are ground together in a ball or roller mill until the solid particles have been reduced to diameters under 10 microns.

What is claimed is:

1. A fungicidal, insecticidal and larvicidal essentially of an effective amount of a compound of the formula $$RS-\underset{S}{\overset{N}{\underset{\|}{\bigvee}}}\underset{S}{\overset{N}{\bigvee}}$$

wherein
R is alkyl of $C_1-C_{10}$, optionally substituted with 1–2 chlorines; alkenyl of $C_3-C_8$, optionally substituted with 1–2 chlorines; cycloalkyl of $C_3-C_{10}$; cycloalkylalkyl of $C_6-C_9$; and $(CH_2)_nR'$, wherein n is 1–3 and R' is phenyl, optionally substituted with $CH_3$, $CH_3O$, $NO_2$, or 1–2 fluorines, chlorines, or bromines and at least one of (a) a surfactant and (b) a solid or liquid diluent.

2. A fungicidal, insecticidal and larvicidal composition of claim 1 wherein R is alkyl of $C_2-C_8$.

3. A fungicidal, insecticidal and larvicidal composition of claim 1 wherein R is alkenyl of $C_3-C_5$.

4. A fungicidal, insecticidal and larvicidal composition of claim 1 wherein R is cycloalkyl of $C_3-C_8$.

5. A fungicidal, insecticidal and larvicidal composition of claim 1 wherein R is $(CH_2)_nR'$ and n is 1 or 2.

6. A fungicidal, insecticidal and larvicidal composition of claim 5 wherein R' is phenyl optionally substituted with 1–2 chlorines.

7. A fungicidal, insecticidal and larvicidal composition of claim 2 wherein R is alkyl of $C_2-C_6$.

8. A fungicidal, insecticidal and larvicidal composition of claim 3 wherein R is alkenyl of $C_3-C_4$.

9. A fungicidal, insecticidal and larvicidal composition of claim 4 wherein R is cycloalkyl of $C_5-C_7$.

10. A fungicidal, insecticidal and larvicidal composition of claim 6 wherein R' is phenyl optionally substituted with one chlorine.

11. A fungicidal, insecticidal and larvicidal composition of claim 7 wherein R is alkyl of $C_2$–$C_3$.

12. A fungicidal, insecticidal and larvicidal composition of claim 8 wherein R is $C_4$ alkenyl.

13. A fungicidal, insecticidal and larvicidal composition of claim 9 wherein R is cycloalkyl of $C_5$–$C_6$.

14. A fungicidal, insecticidal and larvicidal composition of claim 10 wherein R' is phenyl.

15. A fungicidal, insecticidal and larvicidal composition of claim 1 wherein the compound is 2-[(1-methylethyl)thio][1,2,4]-dithiazolo[1,5-b][1,2,4]-dithiazole-4-$S^{IV}$.

16. A fungicidal, insecticidal and larvicidal composition of claim 1 wherein the compound is 2-(ethylthio)[1,2,4]-dithiazolo[1,5-b][1,2,4]-dithiazole-4-$S^{IV}$.

17. A fungicidal, insecticidal and larvicidal composition of claim 1 wherein the compound is 2-[(phenylmethyl)thio][1,2,4]-dithiazolo-[1,5-b][1,2,4]-dithiazole-4-$S^{IV}$.

18. A fungicidal, insecticidal and larvicidal composition of claim 1 wherein the compound is 2-(cyclohexylthio)[1,2,4]-dithiazolo-[1,5-b][1,2,4]-dithiazole-4-$S^{IV}$.

19. A fungicidal, insecticidal and larvicidal composition of claim 1 wherein the compound is 2-[(phenylethyl)thio][1,2,4]-dithiazolo-[1,5-b][1,2,4]-dithiazole-4-$S^{IV}$.

20. A fungicidal, insecticidal and larvicidal composition of claim 1 wherein the compound is 2-(cyclopentylthio)[1,2,4]-dithiazolo-[1,5-b][1,2,4]-dithiazole-4-$S^{IV}$.

21. A fungicidal, insecticidal and larvicidal composition of claim 1 wherein the compound is 2-[(2-methyl-2-propenyl)thio]-[1,2,4]-dithiazolo-[1,5-b][1,2,4]-dithiazole-4-$S^{IV}$.

22. A fungicidal, insecticidal and larvicidal composition of claim 1 wherein the compound is 2-(propylthio)[1,2,4]-dithiazolo[1,5-b][1,2,4]-dithiazole-4-$S^{IV}$.

23. A fungicidal, insecticidal and larvicidal composition of claim 1 wherein the compound is 2-(butylthio)[1,2,4]-ditazolo[1,5-b][1,2,4]-dithiazole-4-$S^{IV}$.

24. A fungicidal, insecticidal and larvicidal composition of claim 1 wherein the compound is 2-[(3-methylbutyl)thio]-dithiazolo[1,5-b][1,2,4]-dithiazole-4-$S^{IV}$.

25. A fungicidal, insecticidal and larvicidal composition of claim 1 wherein the compound is 2-[(2-methylpropyl)thio]-dithiazolo[1,5-b][1,2,4]-dithiazole-4-$S^{IV}$.

26. A method for controlling fungus diseases, and insect and larval pests which comprises applying to locus of infestation a pesticidally effective amount of a compound of the formula

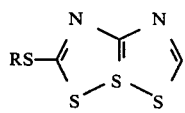

wherein

R is alkyl of $C_1$–$C_{10}$, optionally substituted with 1–2 chlorines; alkenyl of $C_3$–$C_8$, optionally substituted with 1–2 chlorines; cycloalkyl of $C_3$–$C_{10}$; cycloalkylalkyl of $C_6$–$C_9$; and $(CH_2)_nR'$, wherein n is 1–3 and R' is phenyl, optionally substituted with $CH_3$, $CH_3O$, $NO_2$, or 1–2 fluorines, chlorines, or bromines.

27. The method of claim 26 wherein R is alkyl of $C_2$–$C_8$.

28. The method of claim 26 wherein R is alkenyl of $C_3$–$C_5$.

29. The method of claim 26 wherein R is cycloalkyl of $C_3$–$C_8$.

30. The method of claim 26 wherein R is $(CH_2)_nR'$ and n is 1 or 2.

31. The method of claim 30 wherein R' is phenyl optionally substituted with 1–2 chlorines.

32. The method of claim 27 wherein R is alkyl of $C_2$–$C_6$.

33. The method of claim 28 wherein R is alkenyl of $C_3$–$C_4$.

34. The method of claim 29 wherein R is cycloalkyl of $C_5$–$C_7$.

35. The method of claim 31 wherein R' is phenyl optionally substituted with one chlorine.

36. The method of claim 32 wherein R is alkyl of $C_2$–$C_3$.

37. The method of claim 33 wherein R is $C_4$ alkenyl.

38. The method of claim 34 wherein R is cycloalkyl of $C_5$–$C_6$.

39. The method of claim 35 wherein R is phenyl.

40. The method of claim 28 wherein the compound is 2-[(1-methylethyl)thio][1,2,4]-dithiazolo-[1,5-b][1,2,4]-dithiazole-4-$S^{IV}$.

41. The method of claim 28 wherein the compound is 2-(ethylthio)[1,2,4]-dithiazolo[1,5-b]-[1,2,4]-dithiazole-4-$S^{IV}$.

42. The method of claim 28 wherein the compound is 2-[(phenylmethyl)thio][1,2,4]-dithiazolo-[1,5-b][1,2,4]-dithiazole-4-$S^{IV}$.

43. The method of claim 28 wherein the compound is 2-(cyclohexylthio)[1,2,4]-dithiazolo-[1,5-b][1,2,4]-dithiazole-4-$S^{IV}$.

44. The method of claim 28 wherein the compound is 2-[(phenylethyl)thio][1,2,4]-dithiazolo-[1,5-b][1,2,4]-dithiazole-4-$S^{IV}$.

45. The method of claim 28 wherein the compound is 2-(cyclopentylthio)[1,2,4]-dithiazolo-[1,5-b][1,2,4]-dithiazole-4-$S^{IV}$.

46. The method of claim 28 wherein the compound is 2-[(2-methyl-2-propenyl)thio][1,2,4]-dithiazolo-[1,5-b][1,2,4]-dithiazole-4-$S^{IV}$.

47. The method of claim 28 wherein the compound is 2-(propylthio)[1,2,4]-dithiazolo[1,5-b]-[1,2,4]-dithiazole-4-$S^{IV}$.

48. The method of claim 28 wherein the compound is 2-(butylthio)[1,2,4]-dithiazolo[1,5-b]-[1,2,4]-dithiazole-4-$S^{IV}$.

49. The method of claim 28 wherein the compound is 2-[(3-methylbutyl)thio]-dithiazolo[1,5-b]-[1,2,4]-dithiazole-4-$S^{IV}$.

50. The method of claim 28 wherein the 2-[(2-methylpropyl)thio]-dithiazolo[1,5-b][1,2,4]-dithiazole-r-$S^{IV}$.

* * * * *